(12) United States Patent
Shuba

(10) Patent No.: US 10,183,081 B2
(45) Date of Patent: Jan. 22, 2019

(54) USE OF SCINTILLATOR-BASED NANOPARTICLES FOR IN VIVO CONTROL OF LIGHT-SENSITIVE BIOACTIVE MOLECULES

(71) Applicant: Yaroslav M. Shuba, Kyiv (UA)

(72) Inventor: Yaroslav M. Shuba, Kyiv (UA)

( * ) Notice: Subject to any disclaimer, the term of this patent is extended or adjusted under 35 U.S.C. 154(b) by 1567 days.

(21) Appl. No.: 13/761,206

(22) Filed: Feb. 7, 2013

(65) Prior Publication Data

US 2014/0219922 A1  Aug. 7, 2014

(51) Int. Cl.
*A61K 49/04* (2006.01)
*A61K 49/00* (2006.01)
*A61K 41/00* (2006.01)
*B82Y 5/00* (2011.01)

(52) U.S. Cl.
CPC ...... *A61K 49/0428* (2013.01); *A61K 41/0038* (2013.01); *A61K 49/0093* (2013.01); *B82Y 5/00* (2013.01)

(58) Field of Classification Search
CPC ........... A61K 51/00; A61K 49/00; A61K 9/50
USPC .................................................. 424/1.11, 9.6
See application file for complete search history.

(56) References Cited

U.S. PATENT DOCUMENTS

2005/0265922 A1* 12/2005 Nie .................... A61K 49/0002
424/1.11
2007/0218049 A1* 9/2007 Chen ...................... A61K 33/00
424/130.1

OTHER PUBLICATIONS

Xiaohu Gao et al. In vivo molecular and cellular imaging with quantum dots (Current Opinion in Biotechnology 2005, 16, 63-72).*

* cited by examiner

*Primary Examiner* — Michael G. Hartley
*Assistant Examiner* — Jagadishwar R Samala

(57) ABSTRACT

The method for remote, non-invasive in vivo control of the activation of light-sensitive bioactive molecules for the purpose of research or therapy is based on delivering to the required site of the body of nanoparticles along with said light-sensitive bioactive molecules. Nanoparticles' core is made from scintillator material that absorbs X-ray and in response emits visible light; they have biocompatible protective coating and surface targeting agents enabling accumulation at the required site(s) within the body. Irradiation of the site with the highly penetrable X-rays causes nanoparticles to emit visible light which will activate light-sensitive bioactive molecule(s) within this site inducing sought therapeutic effect.

8 Claims, 1 Drawing Sheet

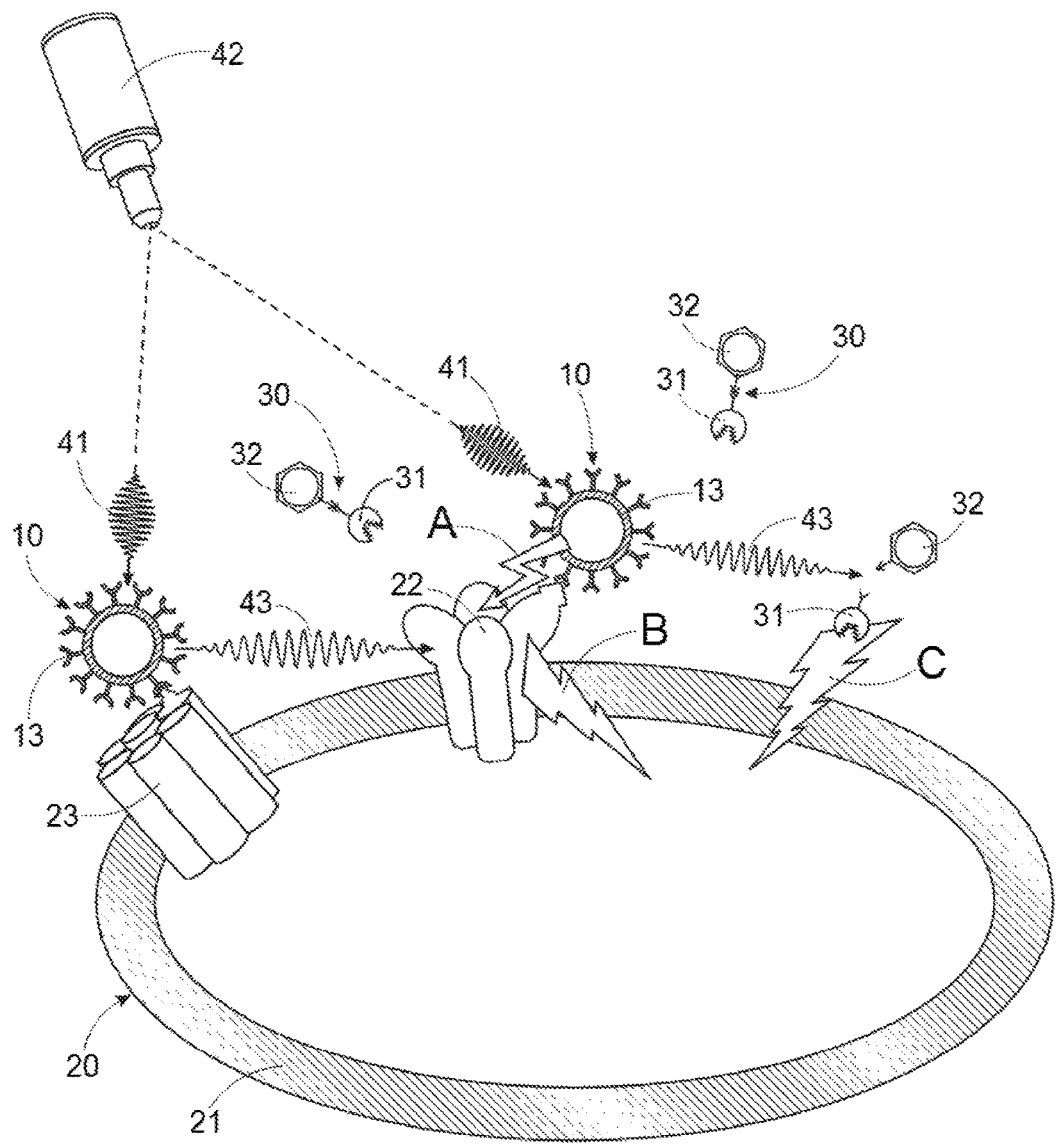

USE OF SCINTILLATOR-BASED NANOPARTICLES FOR IN VIVO CONTROL OF LIGHT-SENSITIVE BIOACTIVE MOLECULES

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

Field of Invention

The present invention relates to the methods of non-invasive control of the activation of light-sensitive bioactive molecules inside live organisms for the purpose of research or therapy.

Discussion of Prior Art

Recent advancements in the development of light-sensitive bioactive molecules and biosensors capable of changing their functional state in response to light irradiation as well as rapid progress in optogenetics provided the researchers invaluable tools for studying numerous biological, physiological and pathophysiological processes and for influencing these processes in the in vitro experimental settings (i.e., in various types of cells and tissues out of organisms) and even in experimental animals in vivo. The light-sensitive bioactive compounds can be artificial or natural.

The first class of artificially synthesized light-sensitive compounds is represented by composite molecules consisting of fluorescence group coupled with active group of which the former serves as a light sensor whereas the latter can bind various exogenous or endogenous bioactive molecules. Upon irradiation with the light of certain wavelength fluorescence group absorbs the quantum of that light and in response emits quantum of light with longer wavelength (i.e., less energetic). The spectrum of light absorption and/or emission can change if active group binds or interacts with other molecules. Such light-sensitive compounds are usually used as reporters of the concentration of certain bioactive molecules or ions within the cells or out of the cells. The best know examples are various types of fluorescent Ca'-sensitive dyes capable of reporting concentration of this physiologically important cation in various cellular compartments.

The second class of synthetic light-sensitive compounds, known as caged compounds (Ellis-Davies (2007) Nat. Methods 4, 619-628), have a photolabile (i.e., subject to photochemical or photophysical reactions) protecting group attached to a significant functional group so as to render the whole molecule biologically inert. Light irradiation removes the protecting group to release the biologically active group. Photorelease of biologically active molecules potentially affords enhanced control over their administration and activation or inhibition of their biological target(s).

Fluorescence chemical groups can be also attached to specific antibodies enabling labeling of various cellular proteins and their visualization.

Finally, identification and cloning of numerous bioluminescent and light-sensitive proteins from various organisms such as, aequorin from luminescent jellyfish, luciferases from bacteria and fireflies, green fluorescent protein (GFP) from jellyfish or sea pansy, channelrhodopsins from green algae, halorhodopsin from halobacteria, etc. gave rise to the whole new avenue of optogenetics (Deisseroth (2011) Nat. Methods 8, 26-29). By inserting recombinant genes for these proteins alone or in combinations with other genes optogenetics allows visualization of various structures and processes as well as controlling cells' behavior in desired direction. For instance, the blue-light sensitive plasma membrane ion channel-forming protein, channelrhodopsin-2 (ChR2, activation wavelength 470 nm), and the yellow light-activated chloride pump halorhodopsin (peak absorbance at 570 nM) expressed together enable multiple-color optical activation and silencing of neural activity with high precision (Rogan & Roth (2011) Pharmacol. Rev. 63, 291-315, Peron & Svoboda (2011) Nat. Methods 8, 30-34). Genetic engineering yielded multiple isoforms of light-sensitive proteins with different optical and functional properties (e.g., Hegemann & Moglich (2011) Nat. Methods 8, 39-42).

Although biomedical research utilizing light-sensitive synthetic compounds and optogenetic approaches is now widespread in the in vitro settings and in vivo animal experimentation, enormous opportunities that such tools provide for diagnostic and therapeutic purposes in humans are largely hampered by technical difficulties for non-invasive delivering of the necessary light stimuli to the required sites within the human body. Because of optical non-transparency of the tissues of higher vertebrates, currently light is delivered in experimental animals only using invasive procedures consisting in implanting portable light source (U.S. Pat. No. 5,445,608, Aug. 1995) or fiber optic light guides which one end is positioned within the targeted area inside the body and another end is sticking out of the body. Besides, permanent implantation of the light-guide reduces versatility of the light-mediated manipulations by only one site to which guide is targeted without the possibility of effectively transferring illumination to other sites on demand dictated by diagnostic or therapeutic purposes. Thus, a novel nanotechnology-based strategy enabling non-invasive delivery of light to any site within the body is required for effective implementation of optical methods in clinics.

Recent progress in the development of nanoscale scintillators (phosphors) which absorb X-rays and emit visible light (U.S. Pat. No. 6,576,156, Jun. 2003; U.S. Pat. No. 8,137,588, Mar. 2012; Nikl (2006) Meas. Sci. Technol. 17, R37-R54; Liu et al (2008) Appl. Phys. Lett. 92, 043901; Morgan et al (2009) Radiat. Res. 171, 236-244) provides a novel approach to overcome the problems of reaching deep tissues by exploiting the high penetrating potential of ionizing X-radiation combined with local emission of visible light. So far this approach is most considered for photodynamic therapy (PDT) of cancer and cancer imaging (U.S. Pat. No. 8,328,785, Dec. 2012; U.S. Pat. No. 7,538,329, May 2009; U.S. Pat. No. 7,018,395, March 2006; Chen & Zhang (2006) J. Nanosci. Nanotechnol. 4, 1159-1166; Liu et al (2008) Appl. Phys. Lett. 92, 043901; Morgan et al (2009) Radiat. Res. 171, 236-244). PDT is based on use of photosensitizers which need to be delivered to pathological tissue and which interaction with light results in the generation of cytotoxic species, such as singlet oxygen ($^1O_2$), free radicals and peroxides, that attack key structural entities within the targeted cells. Using scintillator nanoparticles not only provides the means of photosensitizers activation deep in the tissues, but also enables combination of radiotherapy with photodynamic therapy leading to significant enhancements in therapeutic cytotoxic effect on cancer cells (Morgan et al (2009) Radiat. Res. 171, 236-24). Using another type of penetrable electromagnetic irradiation, radio waves, also enabled remote heating of iron oxide nanoparticles targeted to the endogenous heat-sensitive TRPV1 channel via TRPV1-specific antibodies and stimulation of TRPV1-dependent insulin release from the tumors and lowering of blood glucose in mice (Stanley et al (2012) Science 336, 604-608), indicating that penetrable electromagnetic radiation represents promising strategy for reaching deep tissue layers.

SUMMARY

A method for delivering visible light stimuli to any part inside the body of higher animals including humans with the purpose of activating light-sensitive bioactive compounds or photosensitive recombinant proteins is based on systemic infusion or local injection of scintillator-based nanoparticles. Nanoparticle core is made from scintillator material used to visualize X-ray beams with the protective coating which ensures aqueous solubility, non-toxicity, biocompatibility and prevention of aggregation and non-specific binding. Linkage to nanoparticles of targeting agents such as antibodies, aptamers will further enable directed accumulation of nanoparticles at the required site(s) within the body. Focused irradiation of the site with the highly penetrable X-rays will cause nanoparticles to emit visible light which will activate light-sensitive bioactive molecule(s) within this site causing sought therapeutic effect.

BRIEF DESCRIPTION OF THE DRAWINGS

Various other objects, features and attendant advantages of the present invention will be more fully appreciated and the same becomes better understood from the following detailed description when considered in connection with the accompanying drawings in which like reference characters designate like or corresponding parts wherein:

FIG. 1 shows simplified diagram of the method for remote, non-invasive control of the activity of light-sensitive bioactive molecules or recombinant proteins inside live organism for the purpose of research or therapy and interactions of scintillator-based nanoparticles with microenvironment within tissue. The lightning A indicates activation of foreign light-sensitive protein via resonance energy transfer. The lightnings B and C indicate biological effects of light-sensitive molecules on target cell.

DETAILED DESCRIPTION OF THE INVENTION

Objects and Advantages

The object of the invention is to devise method for non-invasive activation of light-sensitive bioactive molecules or recombinant proteins inside live organisms for the purpose of research or therapy. The proposed solution presents unsurpassed advantages over prior arts in that: 1) it is non-invasive; 2) it can be targeted to any specific site within animal or human body; 3) it can be repeatedly applied.

This object is attained by using a nanoparticle which core is made of scintillator material that absorbs highly penetrable X-rays and in response emits visible light. Currently, huge number of functionalized nanoparticles from various materials which by themselves have diagnostic and/or therapeutic potentials have been proposed and created (Nie & Gao (US 2005/0265922); Wang & Wang (2014) Integr. Biol. (Camb.) 6, 9-26). Likewise, multifunctional light-emitting quantum dots are gaining more and more attention as a new class of fluorescent probes for ex vivo and in vivo molecular and cellular imaging (Gao et al (2005) Curr. Opin. Biotechnol. 16, 63-72). In contrast to these applications, however, scintillator-based nanoparticles in the current context of remote, non-invasive activation of light-sensitive bioactive molecules or recombinant proteins inside live organisms are proposed to be used with only one purpose, namely, to absorb the quantum of X-ray deep inside the tissue and in response reemit quantum of visible light. The advantage of such use is that nanoparticles do not have to enter target cells, as they per se are not aimed to produce any biological effect. For the purpose of just reemitting visible light it is sufficient for them to stay in the extracellular milieu in the vicinity of target cells or to bind to cell surface membrane via targeting agents linked to them. This makes any controls to the observation of whether or not nanoparticles actually enter the cells unnecessary.

Since it is important to obtain as many as possible quanta of emitted visible light per each quantum of absorbed X-ray, the quantum efficiency of phosphor/scintillator material of choice from which nanoparticles to be made becomes an important parameter. High quantum efficiency is also critical for minimizing X-ray irradiation doses of patients. A survey of practically important and/or intensively researched phosphor/scintillator materials show that quantum efficiency can reach 0.5 and in the event of $Ce^{3+}$-doped materials, can be close to 1 (Nikl (2006) Meas. Sci. Technol. 17, R37-R54).

Another important physical parameter of scintillator-based nanoparticles would be an emission spectra which has to maximally coincide with the absorption spectra of light-sensitive bioactive molecules to be used in conjunction with them. For instance, several doped ($LaF_3:Ce^{3+}$, $LuF_3:Ce^{3+}$, $CaF_2:Mn^{2+}$, $CaF_2:Eu^{2+}$, $BaFBr:Eu^{2+}$) and semiconductor ($ZnO$, $ZnS$ and $TiO_2$) scintillator materials have been discussed as potential light sources for use in a nanoparticle-PDT system (Morgan et al (2009) Radiat. Res. 171, 236-244), as their emission spectra can be matched perfectly to the absorption spectra of Photofrin®, fullerenes and $TiO_2$ nanoparticles.

The nanoparticle core is covered with protective coating, which ensures aqueous solubility, non-toxicity, biocompatibility and prevention of aggregation and non-specific binding. Surface of nanoparticle contains conjugated antibodies enabling targeting to specific proteins within the area of interest inside the body. The type of antibody is selected such as to recognize either native surface membrane proteins of targeted cells or recombinant membrane proteins heterologously expressed in targeted cells using in vivo gene transfer technologies. With antibodies against native surface membrane proteins the scintillator nanoparticles can be used to uncage bioactive compounds such as, neurotransmitters, nucleotides, bioactive amines, calcium, lipophilic (i.e., those that can enter the cell via its plasma membrane) or water-soluble (i.e. those that act on the cell surface) pharmacological therapeutic agents, etc. in the vicinity of targeted cells or to activate foreign light-sensitive protein heterologously expressed in target cells. With antibodies against foreign light-sensitive plasma membrane proteins, such as ChR2 and/or halorhodopsin nanoparticles can be used to activate these proteins by direct resonance energy transfer as well as to uncage bioactive compounds in the vicinity of targeted cells. Since ChR2 represents plasma membrane light-activated $Ca^{2+}$-permeable, cationic channel (Nagel et al (2003) Proc. Natl. Acad. Sci. U.S.A. 100, 13940-13945), whereas halorhodopsin is a light-driven ion pump, specific for chloride ions (Lanyi (1990) Physiol. Rev. 70, 319-330), use of scintillator-based nanoparticles will enable remote, X-ray-mediated control of transmembrane ion fluxes in the cells these proteins are heterologously expressed in. Altering transmembrane ion fluxes will in turn affect excitability of electrically excitable cells (neurons, various types of muscle cells), contractility of muscle cells (smooth muscle, cardiac muscle, skeletal muscle) or intracellular ionic homeostasis of non-excitable cells (glial, epithelial, stromal), which can be exploited for scientific or therapeutic purposes.

Preferred Embodiment—FIG. 1

Simplified diagram of the method for remote, non-invasive control of the activity of light-sensitive bioactive molecules or recombinant proteins inside live organism for the purpose of research or therapy is presented in FIG. 1. A method comprises using of a scintillator-based nanoparticle 10 which core part consists of phosphor/scintillator material that absorbs quanta of highly penetrable X-ray 41 and in response emits quanta of visible light 43 of certain wavelength. In particular, the range of scintillator materials can include, but is not limited to, doped rare earth and alkaline earth halides, $LaF_3$:$Ce^{3+}$, $LaF_3$:$TB^{3+}$, $LuF_3$:$Ce^{3+}$, $CaF_2$:$Mn^{2+}$, $CaF_2$:$Eu^{2+}$, $BaFBr$:$Eu^{2+}$, $BaFBr$:$Mn^{2+}$, and semiconductors, ZnO, ZnS and $TiO_2$ (Chen & Zhang (US 2007/0218049 A1); Chen (2008) J. Biomed. Nanotechnol. 4, 369-376).

A method further comprises using separate molecules, such as caged bioactive compound 30 or light-sensitive recombinant protein 22. In the absence of visible light caged bioactive compound 30 or light-sensitive recombinant protein 22 remain biologically inert, but can be converted into biologically active form with sought therapeutic action upon absorption of quantum of visible light. The wavelength of visible light emitted by scintillator-based nanoparticle must maximally match the wavelength of visible light required for uncaging of bioactive compound or activating light-sensitive recombinant protein. Currently, a huge number of caged forms of various classes of biologically active molecules (ions, neurotransmitters, nucleotides, nucleosides, inositols, peptides) have been designed and made, many of which are commercially available (Ellis-Davies (2007) Nat. Methods 4, 619-628). The technologies of organic chemistry for caging essentially any biomolecule or second messenger have now been developed so, the synthesis of caged form of any new molecule or pharmacological agent with required biological or therapeutic activity is technically feasible.

Several protecting chromophores are used in commercially available and under development caged compounds: 1-(2-nitrophenyl)ethyl (NPE) for caging nucleotides, nucleosides and inositols (NPE-ATP, NPE-cAMP, NPE-IP3); 1-(2-nitrophenyl)ethylcarboxy (NPEC), α-carboxy-2-nitrobenzyl (CNB) or 4-methoxy-7-nitroindolinyl (MNI) for caging neurotransmitters (NPEC-AMPA, NPEC-ACPD, NPEC-DCPG, NPEC-dopamine, NPEC-noradrenalin, NPEC-serotonin, CNB-glutamate, CNB-GABA, CNB-carbachol, MNI-kainate, MNI-NMDA); 4,5-dimethoxy-2-nitrobenzyl (DMNB) for caging TRPV1 channel agonist, capsaicin (DMNB-capsaicin). Photolysis of most of these compounds requires irradiation with near-UV wavelengths, with the peak efficiency around 320-360 nm. Of protecting chromophore groups CNB provides the best properties in terms of uncaging rate, quantum efficiency (quantum yield), inertness of photolysis by-product and water solubility, but has the shortest absorption wavelength. Special attention in the context of using in combination with scintillator-based nanoparticles deserve caged compounds synthesized in the form of ruthenium-bispyridine (RuBi) complexes (U.S. Pat. No. 8,063,216, Nov. 2011). RuBi complexes are capable of releasing ligands upon visible light irradiation usually between 400-500 nm, which eliminates deleterious effects of UV light to organs, tissues and cells occurring in the event of UV light-mediated uncaging. Besides, UV and near-UV wavelengths have shorter penetration distance in water solutions compared to visible light reducing the effective area in which uncaging can occur and probability of uncaging. Currently, neurotransmitters, RuBi-Glutamate, RuBi-GABA, RuBi-nicotine, RuBi-serotonin and $K^+$-channel blocker, RuBi-4AP, are commercially available, and ruthenium coordination chemistry opens the way to the design of a wide range of other caged bioactive molecules. The list of biotechnology companies providing caged bioactive compounds includes: Thermo-Fisher Scientific, Tocris Bioscience, Setareh Biotech, Chemcage.

Thus, the range of bioactive compounds which can be remotely, non-invasively released from their caged forms with help of scintillator-based nanoparticles include, but is not limited to, agonists of endogenous cell surface excitatory and inhibitory receptors, glutamate, NMDA, kainate, ACPD, DCPG, nicotine, carbachol, GABA, serotonin, dopamine, noradrenalin, ATP; TRPV1 channel agonist, capsaicin; $K^+$-channel blocker, 4AP. All these bioactive compounds exert their action from extracellular side of the cell making any controls to the observation of whether or not they enter the cells unnecessary. Scintillator-based nanoparticles-assisted release of these compounds within deep tissue layers of live organisms in which respective receptors or channels are expressed can be exploited for remote control of neuronal excitability, muscle contractility, cell electrogenesis, cell secretion, intercellular and intracellular signaling within these layers for the purpose of research or therapy.

A method further comprises systemic infusion of scintillator-based nanoparticles 10 via the blood stream or their local injection into the area of interest inside the body along with administration of a therapeutically effective dose of caged bioactive compound 30. Depending on pharmacokinetics of nanoparticles and of caged bioactive compound, which must be the subject of investigation, caged bioactive compound is administered earlier, simultaneously or certain time after nanoparticles through the same or different administering rout to ensure simultaneous presence of both scintillator-based nanoparticles and caged bioactive compound within the area of interest inside the body. If light-sensitive recombinant protein 22 is used instead of caged bioactive compound appropriate gene transfer technology must be employed to ensure heterologous expression of the protein in the cells within the area of interest at the same time when scintillator-based nanoparticles are present within the same area. In particular, the range of light-sensitive recombinant membrane proteins which activation can be remotely, non-invasively controlled with help of scintillator-based nanoparticles can include, but is not limited to, rhodopsin, ChR2, halorhodopsin and their new genetically engineered isoforms. The concentration of nanoparticles to be systemically or locally administered must be selected such that final concentration of nanoparticles within the area of interest inside the body would ensure reemission of sufficient number of visible light quanta in response to X-ray irradiation for activation of biologically or therapeutically relevant number of active forms of light-sensitive bioactive molecules within that area. The concentration of light-sensitive bioactive molecules to be administered earlier, simultaneously or certain time after nanoparticles through the same or different administering rout must be selected such that the number of active forms of these molecules produced in the area of interest inside the body in response to absorption of visible light quanta would be sufficient to produce sought biological or therapeutic effect on target cells within that area. Alternatively, caged bioactive compound can be directly conjugated to the scintillator-based nanoparticle surface to enable releasing active constituent via resonance energy transfer.

Although technologies of synthesis, surface engineering and functionalizing of nanoparticles from various materials including phosphor/scintillator ones for biomedical applications are largely established, many aspects of the use of these nanoparticles in the context of non-invasive activation of light-sensitive bioactive molecules or recombinant proteins inside live organisms require further in-depth investigation and optimization. These aspects include: selection of concrete phosphor/scintillator material, optimization of nanoparticles size and shape, establishing optimal concentrations of nanoparticles, routs and regimens of their administration, determining nanoparticles pharmacokinetics and pharmacodynamics. This is necessary to ensure maximal X-ray to visible light conversion efficiency of nanoparticles, and safety of their use.

Once both scintillator-based nanoparticles 10 and light-sensitive bioactive compound 30 or recombinant protein 22 are simultaneously present within the area of interest inside the body a method for non-invasive activation of the latter further comprises using X-ray generator 42 capable of producing focused beam of X-ray quanta 41. This beam is directed to the area of interest inside the body. The intensity and time of X-ray exposure must provide reemission of sufficient number of visible light quanta 43 by scintillator nanoparticles upon absorption of X-ray quanta 41 for uncaging bioactive compound or activation of photosensitive recombinant proteins within that area. Free active component of caged compound 31 or activated foreign recombinant photosensitive protein 22 in turn exert desired biological or therapeutic effect on target cells 20 within the area of interest inside the body. Thus, caged bioactive compounds or light-sensitive recombinant proteins in a context of current method are not fulfilling the function of detectors for observing delivered nanoparticles to target cells inside the body, but play the role of active constituents that induce sought biological or therapeutic effect on those cells.

Operation of Invention—FIG. 1

Operations of X-ray, scintillator-based nanoparticle and light-sensitive bioactive molecules in the vicinity of target cell are presented in FIG. 1.

Scintillator-based nanoparticles 10 are delivered to target cells 20 by either direct injection into required site of the body or via infusion to the bloodstream. Depending on their pharmacokinetics, bioactive caged compounds 30 is administered by the same or different rout before, together or after nanoparticles to ensure simultaneous presence of both nanoparticles and caged compounds in the vicinity of target cells. If photosensitive recombinant proteins are used along or instead of caged compounds as therapeutic or research tools, before administering of nanoparticles in vivo gene transfer technologies (Kay (2011) Nat. Rev. Genet. 12, 316-328) are employed to selectively express in target cells foreign photosensitive plasma membrane 21 proteins 22. Antibodies 13 conjugated to nanoparticle permit nanoparticle docking to the native surface proteins 23 of the cell or to the heterologously expressed foreign photosensitive protein 22 thereby increasing targeting specificity. X-rays 41 from X-ray source 42 are focused on target site within the body. Nanoparticle 10 absorbs X-ray and in response emits visible light 43 with the wavelengths, which must coincide with the wavelength for uncaging of caged compound 30 to cause dissociation of its bioactive constituent 31 from photolabile protecting group 32 or to activate photosensitive proteins 22. Free bioactive constituent of caged compound 31 or activated foreign photosensitive protein 22 in turn produce desired biological effect on target cells.

Bioactive compounds which can be remotely, non-invasively released from their caged forms with help of scintillator-based nanoparticles include, but are not limited to, agonists of endogenous cell surface excitatory and inhibitory receptors, glutamate, NMDA, kainate, ACPD, DCPG, nicotine, carbachol, GABA, serotonin, dopamine, noradrenalin, ATP; TRPV1 channel agonist, capsaicin; $K^+$-channel blocker, 4AP. Remote, X-ray-induced, scintillator-based nanoparticles-mediated release of these compounds within deep tissue layers of live organisms in which endogenous receptors or channels sensitive to these compounds are expressed can affect neuronal excitability, muscle contractility, cell electrogenesis, cell secretion, intercellular and intracellular signaling within these layers which can be exploited for research or therapy.

Foreign, photosensitive recombinant membrane proteins heterologously expressed in the certain cell type within the tissue of interest, which activation can be remotely, non-invasively controlled with help of scintillator-based nanoparticles can include, but are not limited to: G-protein-coupled receptor (GPCR), rhodopsin; light-activated $Ca^{2+}$-permeable, cationic channel, ChR2; light-driven ion pump, specific for chloride ions, halorhodopsin, and their new genetically engineered isoforms. Depending on which cell type selected photosensitive protein is expressed in, its X-ray-induced, scintillator-based nanoparticles-mediated activation can induce transmembrane ionic current that can change neuronal excitability, muscle contractility, or disrupt intracellular ionic homeostasis leading to cell death, which can be exploited for research or therapy, such as killing of tumor cells.

Currently a variety of scintillator materials with emission wavelength ranging from violet (~400 nm) to red (~700 nm) light are available (Nikl (2006) Meas. Sci. Technol. 17, R37-R54; Morgan et al (2009) Radiat. Res. 171, 236-244) enabling covering of absorption spectra of any caged compound or photosensitive protein.

To activate several caged compounds and/or photosensitive proteins within the same site inside the body an equal number of scintillator-based nanoparticles with different wavelengths of emitted visible light in response to X-ray irradiation will have to be administered. Alternatively, several fluorescence nanoparticles with single scintillator-based nanoparticle can be co-administered. The use of fluorescence nanoparticles will serve the purpose of reemitting light of progressively longer wavelengths to activate multiple light-sensitive bioactive molecules.

Alternative Embodiments

No alternative embodiments are proposed.

CONCLUSION, RAMIFICATIONS, AND SCOPE OF INVENTION

Thus the reader will see that the proposed invention for using scintillator-based nanoparticles presents the most effective way for in vivo control of light-sensitive bioactive molecules ensuring specific non-invasive targeting of the cells within deep tissue layers of live organisms with the purpose of research or therapy.

The unsurpassed advantages and universality of the proposed method can lead to the development of new therapies and correctional treatments targeting any population of cells, organ or system within human body via localized, X-ray-stimulated released on demand of caged pharmacological agents and other bioactive compounds or activation of photosensitive recombinant proteins.

While the above description contains a number of specifics, these should not be construed as limitations on the scope of the invention, but rather as an exemplification of possible embodiment thereof. This especially relates to the design of composite scintillator-based nanoparticle and type of recombinant photosensitive protein being the object for X-ray-mediated light-induced activation. If the proposed method is to be used for simultaneous X-ray-mediated release of two or more caged compounds and/or activation of photosensitive proteins, co-administering of several scintillator-based nanoparticle with different wavelengths of emitted light should be employed. Alternatively, co-administering of additional fluorescence nanoparticle(s) along with single scintillator-based nanoparticle will be required. In this case fluorescence nanoparticle must be excited by the light wavelength emitted by scintillator-based nanoparticle and in turn emit the light with lower wavelength (i.e., less energetic) which will uncage the second caged compound or activate the second recombinant photosensitive protein. Increasing the number of caged compounds and/or photosensitive proteins to be simultaneously activated by X-ray irradiation will require administering of several scintillator-based nanoparticles or co-administering of several fluorescence nanoparticles with single scintillator-based nanoparticle. The co-administered fluorescence nanoparticles will serve the purpose of reemitting light of progressively longer wavelengths to activate multiple light-sensitive bioactive molecules.

Accordingly, the scope of the invention should be determined not by the embodiment(s) illustrated, but by the appended claims and their legal equivalents.

What I claim as my invention is:

1. A method for non-invasive remote in vivo control of light-sensitive bioactive molecules with the purpose of research and therapy, comprising:
   creating a nanoparticle with biocompatible protective coating and the core part consisting of scintillator material that absorbs highly penetrable X-ray and in response emits visible light of certain wavelength;
      wherein the surface of said nanoparticle bears targeting agent enabling recognition of desired target cells within the area of interest inside the body and interaction with them;
   creating a separate light-sensitive bioactive molecule from a class of caged compounds or photoactivated recombinant proteins which remains biologically inert unless it absorbs the quantum of visible light of the same wavelength as emitted by the core scintillator material of said nanoparticle;
      wherein said light-sensitive bioactive molecule after absorbing visible light converts into active form capable of exerting sought biologic or therapeutic effect on target cells within the area of interest inside the body;
   administering of said light-sensitive bioactive molecule to target cells inside the body by direct injection into the area of interest, via bloodstream or using gene transfer technologies;
   administering of said nanoparticle to target cells inside the body by direct injection into the area of interest or via bloodstream;
      wherein relative timing and administering regimens of said nanoparticle and of said light-sensitive bioactive molecule ensure simultaneous presence of both around the target cells within the area of interest inside the body.

2. The method for non-invasive remote in vivo control of light-sensitive bioactive molecules, as claimed in claim 1, wherein the core part of said nanoparticles is selected from the group of scintillator materials consisting of $LaF_3:Ce^{3+}$, $LaF_3:TB^{3+}$, $LuF_3:Ce^{3+}$, $CaF_2:Mn^{2+}$, $CaF_2:Eu^{2+}$, $BaFBr:Eu^{2+}$, $BaFBr:Mn^{2+}$, $ZnO$, $ZnS$, $TiO_2$.

3. The method for non-invasive remote in vivo control of light-sensitive bioactive molecules, as claimed in claim 1, wherein the light-sensitive bioactive molecule from the class of caged compounds is selected from the group consisting of NPE-ATP, NPEC-AMPA, NPEC-ACPD, NPEC-DCPG, NPEC-dopamine, NPEC-noradrenalin, NPEC-serotonin, CNB-glutamate, CNB-GABA, CNB-carbachol, MNI-kainate, MNI-NMDA, DMNB-capsaicin, RuBi-Glutamate, RuBi-GABA, RuBi-nicotine, RuBi-serotonin, RuBi-4AP, and combinations thereof.

4. The method for non-invasive remote in vivo control of light-sensitive bioactive molecules, as claimed in claim 3, wherein active form of said light-sensitive bioactive molecule from the class of caged compounds regulates neuronal excitability, muscle contractility, cell electrogenesis, cell secretion, intercellular and intracellular signaling of target cells within the area of interest inside the body.

5. The method for non-invasive remote in vivo control of light-sensitive bioactive molecules, as claimed in claim 1, wherein the light-sensitive bioactive molecule from the class of photoactivated recombinant proteins is selected from the group consisting of rhodopsin, ChR2, halorhodopsin, and genetically engineered isoforms thereof.

6. The method for non-invasive remote in vivo control of light-sensitive bioactive molecules, as claimed in claim 5, wherein said light-sensitive bioactive molecule from the class of photoactivated recombinant proteins upon activation regulates neuronal excitability, muscle contractility, or intracellular ionic homeostasis of target cells within the area of interest inside the body.

7. The method for non-invasive remote in vivo control of light-sensitive bioactive molecules, as claimed in claim 1, further comprising focusing X-ray from X-ray emitting device onto the area of interest inside the body containing target cells.

8. The method for non-invasive remote in vivo control of light-sensitive bioactive molecules, as claimed in claim 1, further comprising additional scintillator-based nanoparticle with different wavelengths of emitted light or fluorescence nanoparticle to enable activation of multiple light-sensitive bioactive molecules with different effects on target cells.

* * * * *